​(12) United States Patent
Moskvin et al.

(10) Patent No.: US 8,575,579 B2
(45) Date of Patent: Nov. 5, 2013

(54) MULTI-LEAF COLLIMATOR FOR PROTON BEAM THERAPY

(75) Inventors: Vadim Moskvin, Indianapolis, IN (US); Chee Wai Cheng, Bloomington, IN (US)

(73) Assignee: Indiana University Research and Technololgy Corporation, Indianapolis, IN (US)

( * ) Notice: Subject to any disclaimer, the term of this patent is extended or adjusted under 35 U.S.C. 154(b) by 36 days.

(21) Appl. No.: 13/429,559

(22) Filed: Mar. 26, 2012

(65) Prior Publication Data

US 2013/0072744 A1    Mar. 21, 2013

Related U.S. Application Data

(60) Provisional application No. 61/469,448, filed on Mar. 30, 2011.

(51) Int. Cl.
  *A61N 5/00*  (2006.01)
  *A61N 5/10*  (2006.01)
  *H01J 37/09*  (2006.01)

(52) U.S. Cl.
  USPC .......... 250/505.1; 378/65; 378/147; 378/148; 378/152; 600/436

(58) Field of Classification Search
  USPC ............. 250/505.1; 378/65, 147, 148, 152; 600/436
  See application file for complete search history.

(56) References Cited

U.S. PATENT DOCUMENTS 6,459,762  B1 *  10/2002  Wong et al. ............... 378/65
7,835,502  B2 *  11/2010  Spence et al. ............. 378/143
2009/0041200  A1 *   2/2009  Lu et al. .................. 378/152

OTHER PUBLICATIONS

Moskvin et al., "A Comparison of Neutron Activities Produced in Brass and Tungsten MLC: A Monte Carlo Study", I.J. Radiation Oncology, vol. 78, No. 3, Supplement, 2010, 289, S135-S136.
Staffurth et al., "A Review of the Clinical Evidence for Intensity-modulated Radiotherapy", Clinical Oncology 22 (2010) 643-657.
Xu et al., "A review of dosimetry studies on external-beam radiation treatment with respect to second cancer induction", Physics in Medicine and Biology, 53 (2008) R193-R241.
Cellere et al., "A Review of Ionizing Radiation Effects in Floating Gate Memories", IEEE Transactions on Device and Materials Reliability, vol. 4, No. 3, Sep. 2004, 359-370.
Jemal et al., "Cancer Statisatics, 2010", CA Cancer J Clin 2010;60:277-300.
Wilkinson et al., "Cancer-Radiotherapy Equipment as a Cause of Soft Errors in Electronic Equipment", IEEE Transactions on Device and Materials Reliability, vol. 5, No. 3, Sep. 2005, 449-451.
Daart et al., "Characterization of a mini-multileaf collimator in a proton beamline", Medical Physics, vol. 36, No. 5, May 2009, 1886-1894.
Moskvin et al., "Comment on Comparison of secondary neutron dose in proton therapy resulting from the use of a tungsten alloy MLC or a brass collimator system", [Med. Phys. 38(11), 6248-6256 (2011)], Medical Physics, vol. 39, No. 4, Apr. 2012, 2303-2305.

(Continued)

*Primary Examiner* — Nikita Wells
(74) *Attorney, Agent, or Firm* — Barnes & Thornburg LLP (57) ABSTRACT

A proton beam collimator comprising (a) titanium or (b) stainless steel containing no tungsten or (c) containing no tungsten or brass. The collimator comprises a multi-leaf collimator (MLC). The apparatus further comprises an integrated circuit (IC) mounted adjacent the collimator, the IC subject to exposure to atomic particles, illustratively, neutrons.

15 Claims, 10 Drawing Sheets

(56) References Cited

OTHER PUBLICATIONS

Pijls-Johannesma et al., "Cost-effectiveness of particle therapy: Current evidence and future needs", Radiotherapy and Oncology 89 (2008) 127134.

Shaneyfelt et al., "Enhanced Proton and Neutron Induced Degradation and Its Impact on Hardness Assurance Testing", IEEE Transactions on Nuclear Science, vol. 55, No. 6, Dec. 2008, 3096-3105.

Hengartner et al., "Evaluating Experiments for Estimating the Bit Failure Cross-Section of Semiconductors Using a Colored Spectrum Neutron Beam", Technometrics, Feb. 2008, vol. 50, No. 1, 8-14.

Munshi et al., "Evolution of radiation oncology: Sharp gun, but a blurred target", J Cancer Res Ther, Jan.-Mar. 2010, vol. 6, Issue 1, 3-4.

Peeters et al., "How costly is particle therapy? Cost analysis of external beam radiotherapy with carbon-ions, protons and photons", Radiotherapy and Oncology 95 (2010) 45-53.

Paliwal et al., "IMRT may be used to excess because of its higher reimbursement from medicare", Medical Physics, vol. 31, No. 1, Jan. 2004, 1-3.

Eric J. Hall, "Intensity-Modulated Radiation Therapy, Protons, and the Risk of Second Cancers", Int. J. Radiation Oncology Biol. Phys., vol. 65, No. 1, pp. 1-7, 2006.

Das et al., "Intensity-Modulated Radiation Therapy Dose Prescription, Recording, and Delivery: Patterns of Variability Among Institutions and Treatment Planning Systems", JNCI, vol. 100, Issue 5, Mar. 5, 2008, 300-307.

Eli Glatstein, "Intensity-Modulated Radiation Therapy: The Inverse, the Converse, and the Perverse", Seminars in Radiation Oncology, vol. 12, No. 3 (Jul.), 2002:pp. 272-281.

Fokas et al., "Ion beam radiobiology and cancer: Time to update ourselves", Biochema et Biophysica Acta 1796 (2009) 216-229.

Torikoshi et al., "Irradiation System for HIMAC", J. Radiat. Res.., vol. 48, Suppl. A (2007); A15-A25.

Olsen et al., "Leveraging clinical performance by technological excellence—The case of particle therapy", Radiotherapy and Oncology 95 (2010) 1-2.

Dyer et al., "Neutron-Induced Single Event Effects Testing Across a Wide Range of Energies and Facilities and Implications for Standards", IEEE Transactions on Nuclear Science, vol. 53, No. 6, Dec. 2006, 3596-3601.

Kry et al., "Neutron-induced electronic failures around a high-energy linear accelerator", Medical Physics, vol. 38, No. 1, Jan. 2011, 34-39.

Greene et al., "Pay for Performance: An Overview of the Literature", American Journal of Medical Quality, vol. 24, No. 2, Mar./Apr. 2009, 140-163.

Baro et al., "PENELOPE: An algorithm for Monte Carlo simulation of the penetration and energy loss of electrons and positrons in matter", Nuclear Instruments and Methods in Physics Research B 100 (1995) 31-46.

Christianson et al., "Physician Pay-For-Performance", J Gen Intern Med 2006:21:S9-S13.

Moskvin et al., "Pitfalls of tungsten multileaf collimator in proton beam therapy", Medical Physics, vol. 38, No. 12, Dec. 2011, 6395-6406.

"Proton Therapy: Physical Properties, Beam Production, Interactions in Tissue", Curr Probl Cancer, Jul./Aug. 2010, 257-296.

Huang et al., "Quality of life for head and neck cancer patients treated by combined modality therapy: the therapeutic benefit of technological advances in radiotherapy", Qual Life Res (2010) 19:1243-1254.

Paccagnella et al., "Radiation damage on dielectrics: Single event effects", J. Vac. Sci. Technol. B 27(1), Jan/Feb 2009, 406-410.

Baumann et al., "Radiation-Induced Soft Errors in Advanced Semiconductor Technologies", IEEE Transaction on Device and Materials Reliability, vol. 5, No. 3, Sep. 2005, 305-316.

Bortfield et al., "Realization and Verification of Three-Dimensional Conformal Radiotherapy with Modulated Fields", Int. J. Oncology Biol. Phys., vol. 30, No. 4, pp. 899-908, 1994.

Cheng et al., "Role of Multileaf Collimator in Replacing Shielding Blocks in Radiation Therapy", Int. J. Cancer (Radiat. Oncol. Invest): 96, 385-395 (2001).

Agosteo et al., "Secondary neutron and photon dose in proton therapy", Radiotherapy and Oncology 48 (1998) 293-305.

Howell et al., "Secondary neutron spectra from modern Varian, Siemens, and Elekta linacs with miltileaf collimators", Medicla Physics, Vol. 36, No. 9, Sep. 2009, 4027-4038.

Brenner et al., "Secondary neutrons in clinical proton radiotherapy: A charged issue", Radiotherapy and Oncology 86 (2008) 165-170.

Kallman et al., "Shaping of arbitrary dose distributions by dynamic multileaf collimation", Phys. Med. Biol., 1988, vol. 33, No. 11, 1291-1300.

Tang et al., "Single-event Upsets in Miroelectronics: Fundamental Physics and Issues", MRS Bulletin/Feb. 2003, 111-116.

Soukup et al., "Study of Robustness of IMPT and IMRT for Prostate Cancer Against Organ Movement", Int. J. Radiation Oncology Biol. Phys., vol. 75, No. 2, pp. 941-949, 2009.

Bues et al., "Therapeutic Step and Shoot Proton Beam Spot-Scanning with a Multi-Leaf Collimator: A Monte Carlo Study", Radiation Protection Dosimetry (2005), vol. 115, No. 1-4, pp. 164-169.

Battistoni et al., "The FLUKA code: description and benchmarking", AIP Conf. Proc. 896, 31 (2007): doi: 10.1063/1.2720455, 31-49.

Convery et al., "The generation of intensity-modulated fields for conformal radiotherapy by dynamic collimation", Phys. Med. Biol., 1992, vol. 37, No. 6, 1359-1374.

Tsunadhima et al., "The precision of respiratory-gated delivery of synchrotron-based pulsed beam proton therapy", Physics in Medicine and Biology, 55 (2010) 7633-7647.

Eli Glatstein, "The return of the Snake Oil Salesman", Int. J. Radiation Oncology Biol. Phys., vol. 55, No. 3, pp. 561-562, 2003.

Bortfield et al., "X-ray Field Compensation with Multileaf Collimators", Int. J. Radiation Oncology Biol. Phys., vol. 28, No. 3, pp. 723-730, 1994.

http:www.sciencediredt.com/science/journal/01466453/20? (ICRP Publication 60).

http://www.sciencedirect.com/science/journal/01466453/37/2-4 (ICRP Publication 103).

(FLUKA Monte Carlo code manual) http://www.fluka.org/fluka.php?id=man_onl and http://www.fluka.org/fluka.php?id=manuals&mm2=3.

(MCNPX Monte Carlo code manual) http://mcnpx.lanl.gov/.

* cited by examiner

MULTI-LEAF COLLIMATOR FOR PROTON BEAM THERAPY

This application claims the benefit under 35 U. S. C. §119 (e) of the Mar. 30, 2011 filing date of U.S. Ser. No. 61/469,448. The disclosure of U.S. Ser. No. 61/469,448 is hereby incorporated herein by reference.

Charged particle therapy, especially proton therapy, is a growing treatment modality worldwide. See, for example, McDonald M W, Fitzek M M. Proton Therapy. Curr Probl Cancer. 2010; 34(4):257-96. About twenty more facilities are currently at various stages of design and construction worldwide. Proton therapy has a unique feature of limiting dose deposition to a finite range, thus sparing normal tissues distal to the tumor.

The risk of secondary cancer from neutron dose is a growing concern on long term survivors of cancer, especially pediatric patients. See, for example: Agosteo S, Birattari C, Caravaggio M, Silari M, Tosi G. Secondary neutron and photon dose in proton therapy. Radiother Oncol. 1998; 48(3):293-305; Brenner D J, Hall E J. Secondary neutrons in clinical proton radiotherapy: A charged issue. Radiother Oncol. 2008; 86(2):165-70; Fokas E, Kraft G, An HX, Engenhart-Cabillic R. Ion beam radiobiology and cancer: Time to update ourselves. Biochim Biophys Acta-Rev Cancer. 2009; 1796(2):216-29; and, Hall E J. Intensity-modulated radiation therapy, protons, and the risk of second cancers. Int J Radiat Oncol Biol Phys. 2006; 65(1):1-7. The dose for the distant areas of the body is determined, in proton therapy, by secondary neutrons generated in interaction of protons with the beam shaping device, for example, an aperture crafted from brass.

The reported (Jemal A, Siegel R, Xu J Q, Ward E. Cancer Statistics, 2010. CA-Cancer J Clin. 2010; 60(5):277-300) decline in treatment reimbursement on a nearly constant cancer incidence rate has stimulated interest in cost efficient mechanisms in the operation of proton facilities. See, for example: Peeters A, Grutters J P C, Pijls-Johannesma M, Reimoser S, De Ruysscher D, Severens J L, et al. How costly is particle therapy? Cost analysis of external beam radiotherapy with carbon-ions, protons and photons. Radiother Oncol. 2010; 95(1):45-53; Olsen D R, Overgaard J. Leveraging clinical performance by technological excellence—The case of particle therapy. Radiother Oncol. 2010; 95(1):1-2; and, Pijls-Johannesma M, Pommier P, Lievens Y. Cost-effectiveness of particle therapy: Current evidence and future needs. Radiother Oncol. 2008; 89(2):127-34. The multi-leaf collimator (hereinafter sometimes MLC) provides an attractive alternative to brass apertures for use in proton facilities. However, commercially available MLCs for megavoltage therapy are made from tungsten. It has been reported that the measured neutron dose from tungsten micro-MLCs is in the range 1.5-1.8 times higher than that from brass apertures. See, for example: Daartz J, Bangert M, Bussiere M R, Engelsman M, Kooy H M. Characterization of a mini-multileaf collimator in a proton beamline. Med Phys. 2009; 36(5):1886-94; Moskvin V P, Cheng C, Nichihporov D, Das I. A Comparison of Neutron Activities Produced in Brass and Tungsten MLC: A Monte Carlo Study. Int J Radiat Oncol Biol Phys. 2010; 78(3):S135-S6; and, Moskvin V P, Cheng C, Das I. Pitfalls of tungsten multileaf collimator: Proton therapy; Med Phys. 2011; 38(12):6395-6406. In a preliminary study with Monte Carlo simulation to compare the neutron production of a tungsten MLC with the neutron production of a brass aperture, it was found that tungsten produces a higher neutron dose, about 1.6 times that from a brass aperture. See, Moskvin V P, Cheng C, Nichihporov D, Das I. A Comparison of Neutron Activities Produced in Brass and Tungsten MLC: A Monte Carlo Study. Int J Radiat Oncol Biol Phys. 2010; 78(3):S135-S6. In addition, a study of the activation of a tungsten MLC and its impacts on the electronics inside a proton nozzle concluded, inter alia, that tungsten is not the optimal material for an MLC in proton therapy. See also, Moskvin, Cheng, and Das: Pitfalls of tungsten multileaf collimator: Proton therapy; Medical Physics, Vol. 38, No. 12, December 2011, 6395-6406.

There remains a clinical need to reduce patient exposure to secondary neutron emissions in order to reduce the risk of secondary cancers. There also remains a clinical need to provide a method of proton beam shaping which is more cost efficient that that available with a brass aperture.

According to an aspect of the invention, a proton beam collimator is made from titanium.

According to an aspect of the invention, a proton beam collimator is made from stainless steel including no tungsten.

According to an aspect of the invention, a proton beam collimator is made from a material containing no tungsten and no brass.

Illustratively according to these aspects, the collimator comprises a multi-leaf collimator (MLC).

Further illustratively according to these aspects, the collimator comprises an integrated circuit (IC) mounted adjacent the collimator. The IC is subject to exposure to atomic particles. Further illustratively the atomic particles are neutrons.

The invention may best be understood by referring to the following detailed description and accompanying drawings which illustrate the invention. In the drawings.

It is believed that the development of a new type of MLC system based upon reduction of the secondary neutron dose will benefit proton therapy. It is also believed that the design of an MLC based upon reduction of the secondary neutron dose will facilitate new approaches for cancer treatment planning, such as, for example, a dynamic MLC to account for tumor motion.

Preliminary data suggests that titanium alloys may be the optimal materials for MLCs applicable to proton therapy. It is believed that titanium alloys will minimize the secondary neutron doses to patients while providing field shaping equivalent to, for example, a brass aperture.

To achieve a multi-leaf collimator for reducing the neutron dose generated by a proton beam, the engineering design of multi-leaf collimators for proton therapy must be investigated. This involves determining the optimal material for an MLC and the optimal geometry for MLC to minimize the dose to a patient from secondary neutrons. Monte Carlo simulations of the primary proton beam and secondary neutron transport are used to advance these investigations. The radiation tolerance of electronic circuits used for MLC controllers and the electronic placement for minimization of probability of soft errors caused by secondary neutron fluence must also be investigated, along with the mechanical designs of MLCs and the cost of the MLC manufacturing.

The utilization in proton therapy of beam shaping devices which reduce secondary neutron doses to patients will improve the quality of patient care and reduce the cost of operation. Ultimately, the use of such devices will improve the efficacy of the clinic operation, increase the survival ratio, and reduce secondary cancer risk. The development of beam shaping devices such as, for example, dynamic MLCs (hereinafter sometimes DMLCs) for proton therapy will permit adaptive field shaping to account for tumor motion.

Growing population, the decline in treatment reimbursement (see, for example: Greene S E, Nash D B. Pay for Performance: An Overview of the Literature. Am J Med Qual. 2009; 24(2):140-63; and, Christianson J B, Knutson D J, Mozze R S. Physician pay-for-performance—Implementation and research issues. J Gen Intern Med. 2006; 21:S9-S13), and nearly constant cancer incidence rates (Jemal A, Siegel R, Xu J Q, Ward E. Cancer Statistics, 2010. CA-Cancer J Clin. 2010; 60(5):277-300) result in very unfavorable financial outlooks for high-end scientific clinical modalities. The need to develop cost-efficient mechanisms in the operation of a proton facility (Peeters A, Grutters J P C, Pijls-Johannesma M, Reimoser S, De Ruysscher D, Severens J L, et al. How costly is particle therapy? Cost analysis of external beam radiotherapy with carbon-ions, protons and photons. Radiother Oncol. 2010; 95(1):45-53; Olsen D R, Overgaard J. Leveraging clinical performance by technological excellence—The case of particle therapy. Radiother Oncol. 2010; 95(1):1-2; Pijls-Johannesma M, Pommier P, Lievens Y. Cost-effectiveness of particle therapy: Current evidence and future needs. Radiother Oncol. 2008; 89(2):127-34), compatible with the conventional megavoltage photon machine, is apparent.

Proton therapy has a unique feature of limiting dose deposition to a finite range, thus leaving tissues distal to the tumor unaffected. There is a clinical need to provide a method of proton beam shaping which is more cost efficient compared to the current method of proton beam shaping with a brass aperture. MLCs provide an attractive alternative to the brass aperture. Charged particle therapy, especially proton therapy is a growing treatment modality worldwide. See, for example, McDonald M W, Fitzek M M. Proton Therapy. Curr Probl Cancer. 2010; 34(4):257-96. About twenty more facilities are currently at various stages of design and construction worldwide. The usage of MLCs rather than brass apertures will decrease the total treatment time, which is of benefit to the patient, and improve patient throughput for a clinic, as well as eliminating the cost of the aperture manufacturing.

Numerous studies on MLCs in the early 1990s (see, for example: Bortfeld T, Boyer A L, Schlegel W, Kahler D L, Waldron T J. Realization and verification of 3-dimentional conformal radiotherapy with modulated fields. Int J Radiat Oncol Biol Phys. 1994; 30(4):899-908; Bortfeld T R, Kahler D L, Waldron T J, Boyer A L. X-ray field compensation with multileaf collimators. Int J Radiat Oncol Biol Phys. 1994; 28(3):723-30; Convery D J, Rosenbloom M E. The generation of intensity-modulated fields for conformal radiotherapy by dynamic collimation. Phys Med Biol. 1992; 37(6):1359-74; and, Kallman P, Lind B, Eklof A, Brahme A. Shaping of arbitrary dose distributions by dynamic multileaf collimation. Phys Med Biol. 1988; 33(11):1291-300) led to considerable use of intensity modulated radiation therapy (hereinafter sometimes IMRT) with megavoltage photon beams ten years later. Despite concerns regarding risks versus benefits (see, for example: Das I J, Cheng C W, Chopra K L, Mitra R K, Srivastava S P, Glatstein E. Intensity-modulated radiation therapy dose prescription, recording, and delivery: Patterns of variability among institutions and treatment planning systems. J Natl Cancer Inst. 2008; 100(5):300-7; Glatstein E. Intensity-modulated radiation therapy: The inverse, the converse, and the perverse. Semin Radiat Oncol. 2002; 12(3):272-81; Glatstein E. The return of the snake oil salesmen. Int J Radiat Oncol Biol Phys. 2003; 55(3):561-2; Munshi A, Agarwal J P. Evolution of radiation oncology: Sharp gun, but a blurred target. J Canc Res Ther. 2010; 6(1):3-4; Staffurth J, Board R D. A Review of the Clinical Evidence for Intensity-modulated Radiotherapy. Clin Oncol. 2010; 22(8):643-57; and, Huang T L, Tsai W L, Chien C Y, Lee T F, Fang F M. Quality of life for head and neck cancer patients treated by combined modality therapy: the therapeutic benefit of technological advances in radiotherapy. Qual Life Res. 2010; 19(9):1243-54), IMRT with MLC has become the treatment of choice for over 50% of disease sites, perhaps partially due to higher reimbursement for the treatments (see, for example, Paliwal B R, Brezovich I A, Hendee W R. IMRT may be used to excess because of its higher reimbursement from medicare. Med Phys. 2004; 31(1):1-3). MLC itself had been shown as an alternative method of photon beam shaping to cerrobend blocks in 3-D conformal therapy, reducing the dose to critical structures (See, for example: Staffurth J, Board R D. A Review of the Clinical Evidence for Intensity-modulated Radiotherapy. Clin Oncol. 2010; 22(8):643-57; and, Cheng C W, Das I J, Steinberg T. Role of multileaf collimator in replacing shielding blocks in radiation therapy. Int J Cancer. 2001; 96(6):385-95). Clinical experience with custom stainless steel MLC in carbon ion therapy appears to support implementation of MLC in particle therapy for routine practice. See, for example, Torikoshi M, Minohara S, Kanematsu N, Komori M, Kanazawa M, Noda K, et al. Irradiation system for HIMAC. J Radiat Res. 2007; 48:A15-A25. A few recent preliminary studies have focused on possible implementation of a commercial MLC made from tungsten for field shaping in proton therapy. See, for example: Daartz J, Bangert M, Bussiere M R, Engelsman M, Kooy H M. Characterization of a mini-multileaf collimator in a proton beamline. Med Phys. 2009; 36(5):1886-94; and, Bues M, Newhauser W D, Titt U, Smith A R. Therapeutic step and shoot proton beam spot-scanning with a multi-leaf collimator: A Monte Carlo study. Radiat Prot Dosim. 2005; 115(1-4):164-9.

The risk of secondary cancer from neutrons is a growing concern. See, for example: Agosteo S, Birattari C, Caravaggio M, Silari M, Tosi G. Secondary neutron and photon dose in proton therapy. Radiother Oncol. 1998; 48(3):293-305; Brenner D J, Hall E J. Secondary neutrons in clinical proton radiotherapy: A charged issue. Radiother Oncol. 2008; 86(2):165-70; Fokas E, Kraft G, An HX, Engenhart-Cabillic R. Ion beam radiobiology and cancer: Time to update ourselves. Biochem Biophys Acta-Rev Cancer. 2009; 1796(2):216-29; and, Hall E J. Intensity-modulated radiation therapy, protons, and the risk of second cancers. Int J Radiat Oncol Biol Phys. 2006; 65(1):1-7. The dose for the distant areas of the body is determined, in proton therapy, by secondary neutrons generated by interaction of proton beams with the beam shaping device, the brass aperture. The superiority of proton therapy in terms of dose shaping and sparing of healthy tissues will likely lead to an increase in the percentage of pediatric patients undergoing particle therapy. There is a clinical need to reduce secondary neutron doses to patient to reduce the risk of secondary cancer.

The replacement of brass apertures with MLC technology from megavoltage external beams in proton therapy has been carefully examined. The MLC appears capable of providing lateral dose falloff compatible to brass aperture. However, the secondary neutron dose from a tungsten micro-MLC is found to be about 1.5-1.8 times higher than that experienced with a brass aperture (see, for example: Daartz J, Bangert M, Bussiere M R, Engelsman M, Kooy H M. Characterization of a mini-multileaf collimator in a proton beamline. Med Phys. 2009; 36(5):1886-94; Moskvin V P, Cheng C, Nichihporov D, Das I. A Comparison of Neutron Activities Produced in Brass and Tungsten MLC: A Monte Carlo Study. Int J Radiat Oncol Biol Phys. 2010; 78(3):S135-S6; and, Moskvin V P, Cheng C, Das I. Pitfalls of tungsten multileaf collimator: Proton therapy; Med Phys. 2011; 38(12):6395-6406.) raising concern about the higher risk of secondary malignancy when a tungsten MLC is used instead of a brass aperture.

Preliminary data suggests that the utilization of the commercial tungsten MLC may not be the best option for proton beam therapy. With a tungsten MLC, the secondary neutron dose to the patient is at least 1.6 times higher than that from the brass aperture of the same thickness (6.5 cm in preliminary studies). The ambient dose equivalent, H*(10), 10 cm downstream from the tungsten MLC is about 22.3 mSv·Gy$^{-1}$ while the ambient dose equivalent, H*(10), 10 cm downstream from the brass aperture is about 14 mSv·Gy$^{-1}$. Thus, there may be increased risk of secondary cancer from neutrons using a tungsten MLC in proton beam therapy.

The activity of a unit volume of the irradiated brass aperture reaches $5.3 \cdot 10^4$ Bq·cm$^{-3}$ at the end of the last treatment for a 40-fraction treatment course. The activity decreases to $1.4 \cdot 10^2$ Bc·cm$^{-3}$ after 24 hours of cooling. After 40 days in storage, the activity decreases by 6.2 times to 23.4 Bq·cm$^{-3}$. The cooling of the brass aperture in one year will bring the activity to the background level.

For a tungsten MLC, the buildup of activity is about 3.4 times higher than that for a brass aperture at the end of the same 40-fraction treatment, assuming 30 patients are treated using the MLC. The residual activity decreases by a factor of 2 after 40 days of MLC cooling, to an activity of $1.78 \cdot 10$ Bq·cm$^{-3}$, which is about 7600 times higher than the corresponding activity for the brass aperture. The daily utilization of the MLC also leads to buildup of activity with time. The estimated activity per unit volume of a tungsten MLC is about $1.2 \cdot 10^6$ Bq·cm$^{-3}$ after one year of operation. The contribution of $^{181}_{74}$W is about 12.5% to the total activity. Since the half-life of $^{181}_{74}$W is 121.2 days, its activity reaches saturation in about 2 years. However, the overall activity will continue to increase due to the presence of $^{179}_{73}$Ta, whose half-life is 1.82 years. Thus, at the end of an operating cycle, a tungsten MLC will require prolonged storage for cooling.

From these data, it appears that proton beam therapy using tungsten MLCs may expose patients and operating staff to double the secondary cancer risk from secondary neutron yield due to activation of the tungsten MLC.

Additionally, the risk of mistreatment may also increase due to higher probability of the MLC controller malfunctioning owing to exposure of integrated circuits (hereinafter sometimes ICs) in the controller to the secondary neutron field. Further concerns are raised for safety, disposal and salvaging in the utilization of MLC material at the end of an operating cycle due to tritium accumulation within the MLC material.

Patient throughput in clinical settings is improved by eliminating the time associated with switching apertures between patients. Waiting time associated with aperture manufacturing is also eliminated. The application of MLCs in proton beam facilities will eliminate the cost of aperture machines. The utilization of the beam shaping device, which will reduce secondary neutron doses to patients compared to current beam aperture practice may help to increase the survival ratio and reduce secondary cancer risk. Combination of the spot scanning proton beam with the MLC as an additional beam shaping device and to reduce the dose penumbra will further reduce the secondary neutron dose to the patient. Another significant concern in radiation therapy, including proton beam therapy, is based on the tumor motion. See, for example: Soukup M, Sohn M, Yan D, Liang J, Alber M. Study Of Robustness Of IMPT And IMRT For Prostate Cancer Against Organ Movement. Int J Radiat Oncol Biol Phys. 2009; 75(3): 941-9; and, Tsunashima Y, Vedam S, Dong L, Umezawa M, Baiter P, Mohan R. The precision of respiratory-gated delivery of synchrotron-based pulsed beam proton therapy. Phys Med Biol. 2010;55(24):7633-47). The long term impact of the MLC system for proton therapy is the facilitation of the clinical research and development of an innovative beam shaping device, namely, a DMLC for proton therapy, which allows adaptive field shaping to account for tumor motion.

A proton beam produces less spallation neutrons in materials with relatively lower atomic numbers. Titanium appears to be a useful material for MLC applicable to proton therapy. The use of titanium alloys reduces the secondary neutron dose to the patient while providing field shaping on the scale of the brass aperture.

Figure 1A:
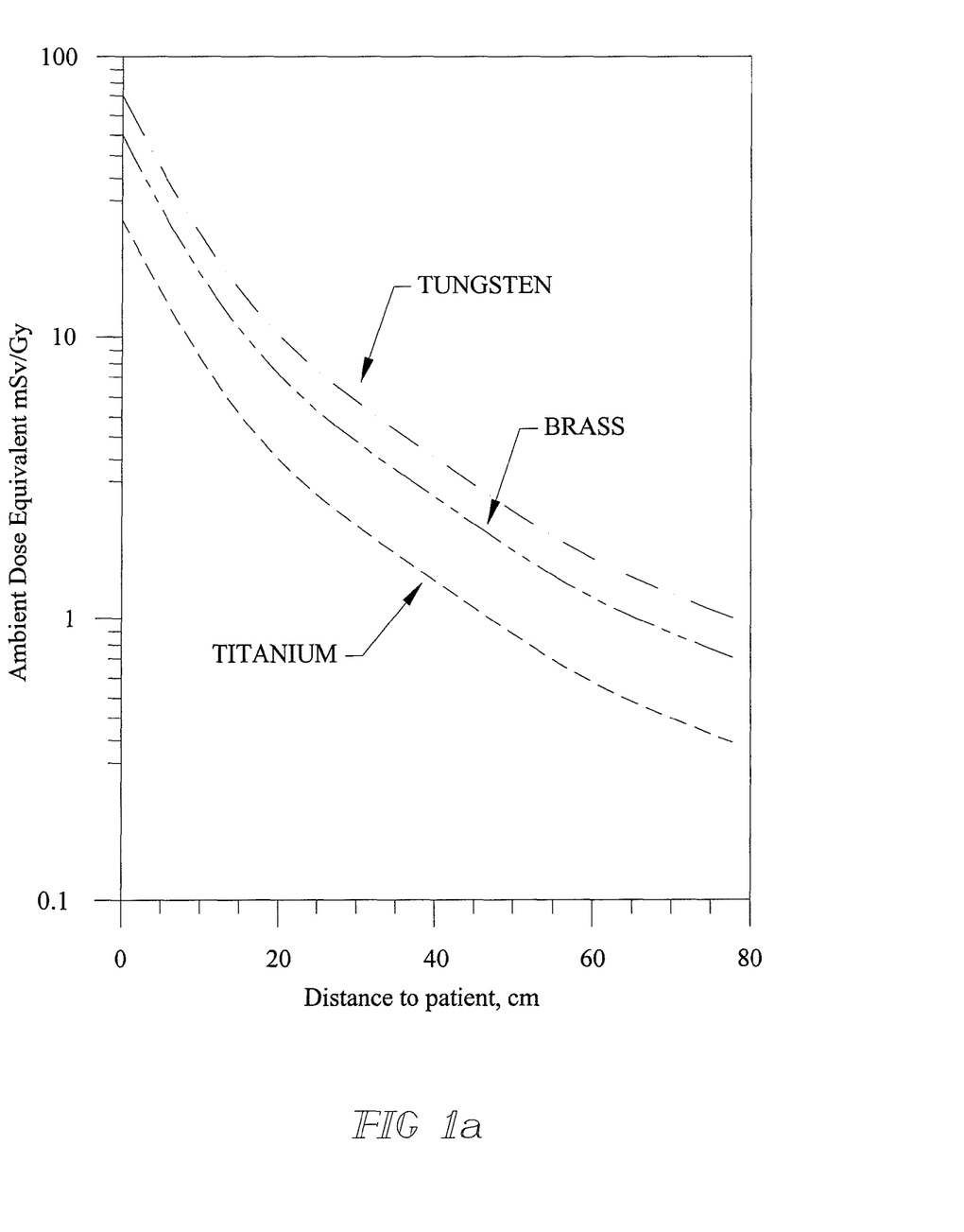
FIG. 1 illustrates ambient dose equivalent H*(10) pSv per unit dose, Gy, delivered by incident proton beam, from secondary neutrons generated by 200 MeV proton beam in MLCs constructed from various material. H*(10) is given as a function of distance from the MLC to a patient. (Ambient dose equivalent for a given distance represents dose that a person may get at this distance. The patient usually is treated at 5 cm distance from the aperture. That patient will be at similar distance from an MLC)
Figure 1B:
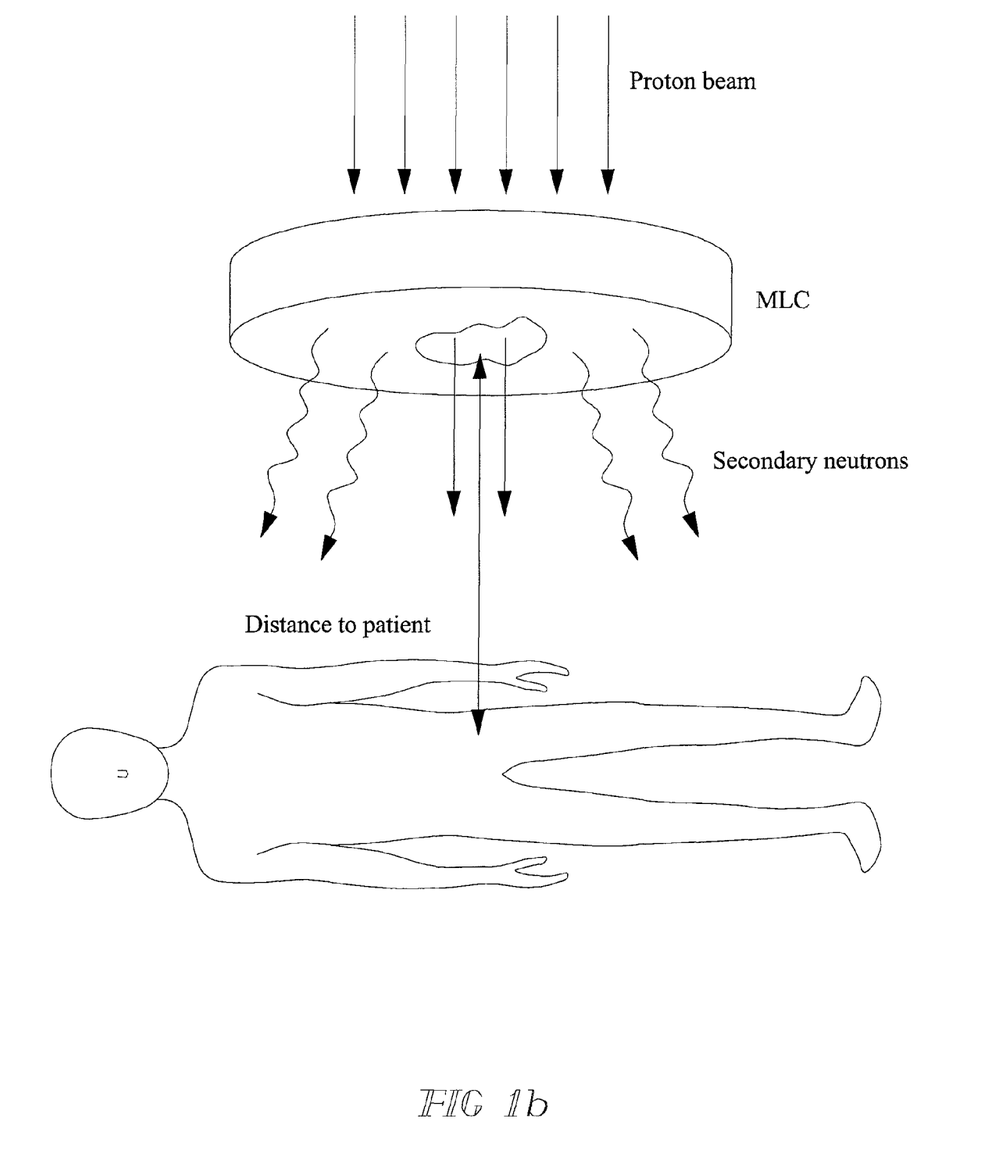
Figure 2:
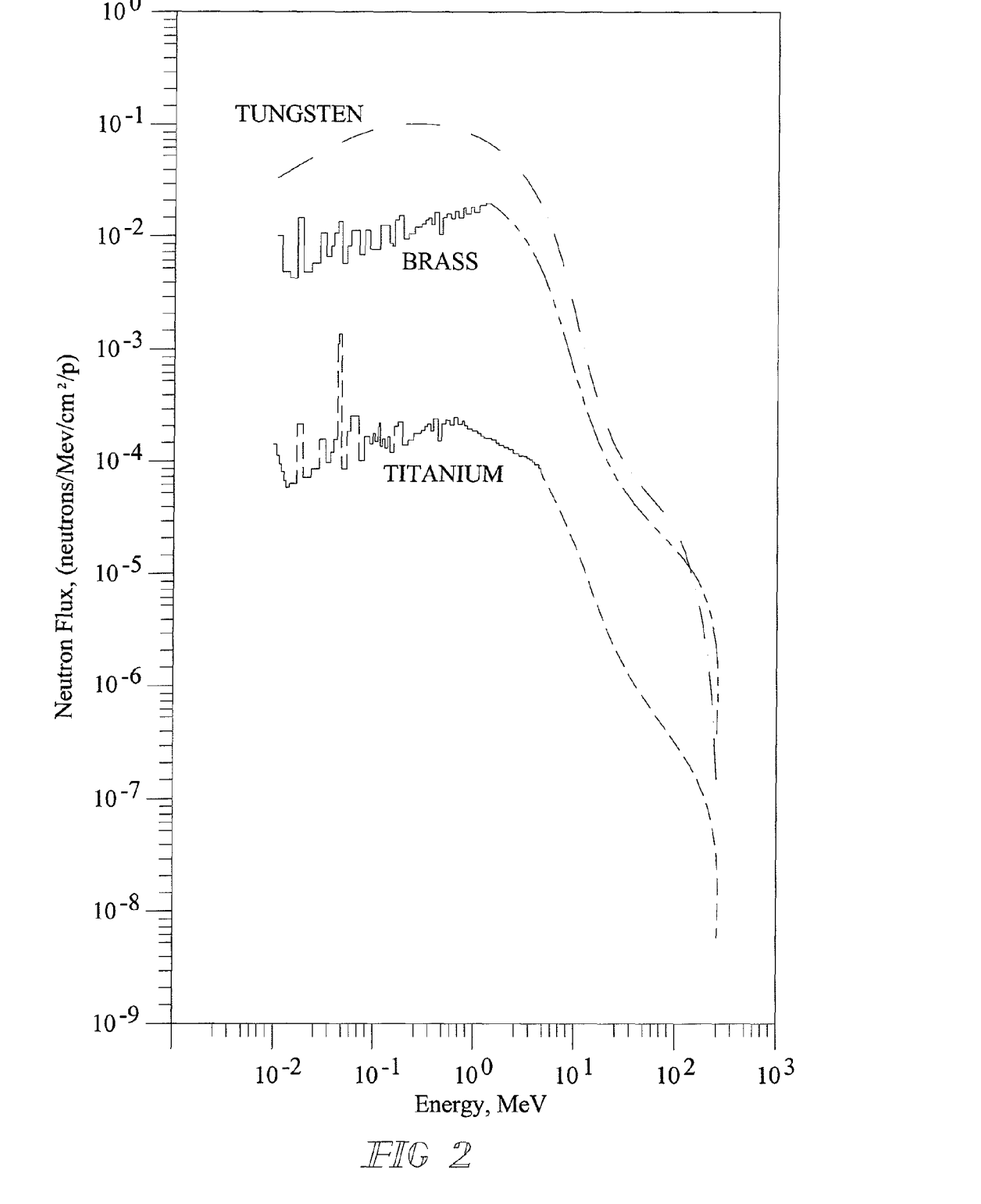
FIG. 2 illustrates energy distribution of neutrons generated by 200 MeV proton beam in MLCs constructed from various materials.
Figure 5:
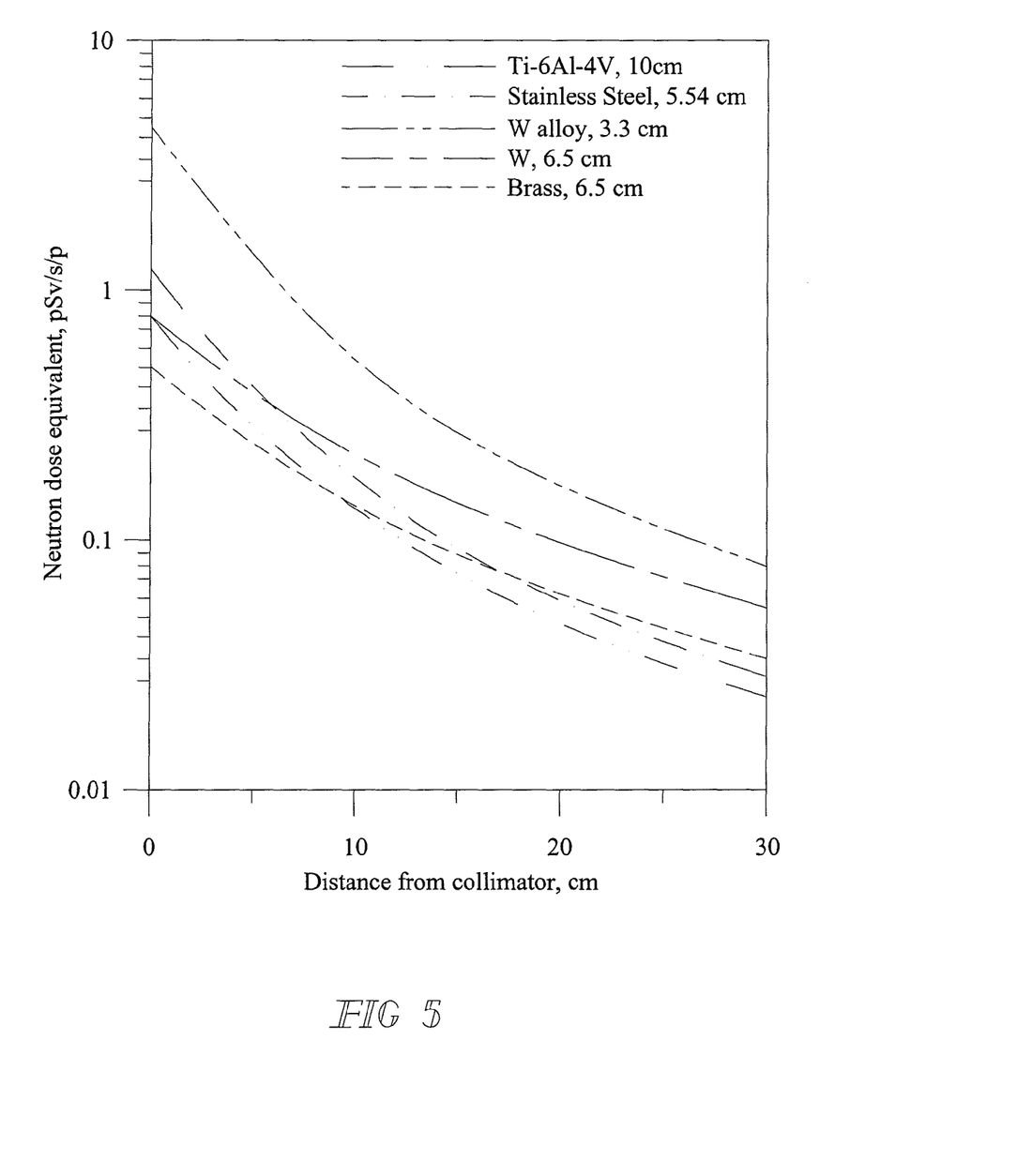
FIG. 5 illustrates neutron dose equivalents for various collimator materials.

The analysis of the cross-sections of reactions producing spallation neutron for various materials shows that neutron yield dramatically decreases for low atomic number materials. Referring to FIGS. 1 and 5, the dose to the patient, H*(10), from secondary neutrons produced in titanium MLCs is roughly an order of magnitude less than those from tungsten MLCs and about three times less than from brass apertures of the same mass thickness as titanium MLC. The thicknesses of materials were selected assuming the absorption of maximum of proton beam energy utilized in practice. Referring to FIGS. 2 and 4, the data on secondary neutron spectra suggests that titanium produces significantly fewer neutrons of high quality factor than tungsten or brass beam shaping devices (MLCs or apertures). Low atomic number materials like titanium or stainless steel are preferred options to tungsten or brass for a MLC. Stainless steel may not be an optimal material for MLC production, owing to its mechanical properties. The titanium MLC appears to be a more attractive option. It may reduce the secondary neutron dose to the patient by as much as an order of magnitude compared to the brass aperture.

To test this hypothesis, a set of Monte Carlo simulations are conducted for a set of the titanium alloys with the FLUKA code. For a FLUKA code description, see, for example: Battistoni G, Muraro S, Sala P R, Cerutti F, Ferrari A, Roesler S, et al. The FLUKA code: Description and benchmarking. M. Albrow, R. Raja editors. Proceedings of the Hadronic Shower Simulation Workshop 2006, Fermilab 6-8 Sep. 2006, AIP Conference Proceedings. 2007; 896:31-49; and, Ferrari A, Sala P R, Fasso A, Ranft J. FLUKA: a multi-particle transport code. CERN 2005-10 (2005), INFN/TC_05/11, SLAC-R-773. FLUKA is a fully integrated particle physics Monte Carlo simulation package widely used in experimental physics and engineering, shielding, detector design, dosimetry, medical physics and radiobiology. Monte Carlo simulation is a world-recognized substitution that reduces the cost of R&D work substantially. MCNPX is used for cross-reference and comparison. See, for example, Hughes H, Prael R, Little R. MCNPX—The LAHET/MCNP Code Merger, X-Division Research Note XTM-RN(U)97-012, LA-UR-97-4891 Los Alamos National Laboratory; 1997.

The simulations to determine the geometrical parameters of a titanium MLC, to evaluate the proton scattering and dose penumbra in phantom, and to compare these to a conventional brass aperture are carried out. Neutron fluences from the proton beam nozzle component are also evaluated based on Monte Carlo simulations.

Electronic devices placed in low dose ionizing radiation fields are subject to so-called soft errors or single event upset (hereinafter sometimes SEU). See, for example: Hengartner N W, Takala B E, Michalak S E, Wender S A. Evaluating experiments for estimating the bit failure cross-section of semiconductors using a colored spectrum neutron beam. Technometrics. 2008; 50(1):8-14; Tang H H K, Rodbell K P. Single-event upsets in microelectronics: Fundamental physics and issues. MRS Bull. 2003; 28(2):111-6; Cellere G, Paccagnella A. A review of ionizing radiation effects in floating gate memories. IEEE Trans Device Mater Reliab. 2004; 4(3):359-70; Baumann R C. Radiation-induced soft errors in advanced semiconductor technologies. IEEE Trans Device Mater Reliab. 2005; 5(3):305-16; and, Dyer C, Hands A, Ford K, Frydland A, Truscott P. Neutron-induced single events affect testing across a wide range of energies and facilities and have implications for standards. IEEE Trans Nucl Sci. 2006; 53(6):3596-601. One random intruded particle can generate a signal large enough to disrupt normal device operation without permanent device damage. Because of the random nature, SEU may not be duplicated. The result of a soft error is a single bit change, e. g., a stuck bits flip observed in synchronous dynamic random access memories (hereinafter sometimes SDRAMs). See, for example, Cellere G, Paccagnella A. A review of ionizing radiation effects in floating gate memories. IEEE Trans Device Mater Reliab. 2004; 4(3):359-70.

A growing concern in electronics is the micro-dose effect. The further miniaturization of the devices makes them more sensitive to ionizing radiation. This trend is reported for electronics used for CT-scanners on rails. See, for example, Kry S F, Johnson J L, White R A, Howell R M, Kudchadker R J, Gillin M T. Neutron-induced electronic failures around a high-energy linear accelerator. Med Phys. 2011; 38(1):34-9. ICs typically contain numerous low and high-atomic number materials. This fact alone may impact the radiation hardness of ICs in high-energy particle environments or neutron fields. See, for example: Paccagnella A, Gerardin S, Cellere G. Radiation damage on dielectrics: Single event effects. J Vac Sci Technol B. 2009; 27(1):406-10; and, Shaneyfelt M R, Felix J A, Dodd P E, Schwank J R, Dalton S M, Baggio J, et al. Enhanced Proton and Neutron Induced Degradation and Its Impact on Hardness Assurance Testing. IEEE Trans Nuci Sci. 2008; 55(6):3096-105. Typical commercial ICs placed at the head of a proton beam gantry and used in MLC operations for megavoltage linear accelerators (hereinafter sometimes LINACs) contain boron, tungsten, and aluminum. Low energy neutrons cause high rates of SEU through micro-dose effects in elements of such ICs due to Li and He ion transport from the neutron capture reaction $_5^{10}B(n,\alpha)_3^7Li$ in lower inter-metal dielectric layers of such ICs. See, for example, Wilkinson J D, Bounds C, Brown T, Gerbi B J, Peltier J. Cancer-radiotherapy equipment as a cause of soft errors in electronic equipment. IEEE Trans Device Mater Reliab. 2005; 5(3):449-51. Our calculation with the FLUKA Monte Carlo code illustrate that the neutron dose equivalent measured and calculated for radiotherapy megavoltage machines with an MLC varies from 1 to 3 mSv·Gy$^{-1}$, depending on the machine manufacturer (see, for example, Howell R M, Kry S F, Burgett E, Hertel N E, Followill D S. Secondary neutron spectra from modern Varian, Siemens, and Elekta linacs with multileaf collimators. Med Phys. 2009; 36(9):4027-38), at a distance of 20 cm from the beam axis at the isocenter level. The estimated and measured data on neutron dose equivalent for proton therapy varies from 10 mSv·Gy$^{-1}$ for a double scattering beam to <0.1 mSv·Gy$^{-1}$ for a scanning beam (see, for example, Xu X G, Bednarz B, Paganetti H. A review of dosimetry studies on external-beam radiation treatment with respect to second cancer induction. Phys Med Biol. 2008; 53(13):R193-R241) at the patient level.

Figure 3:
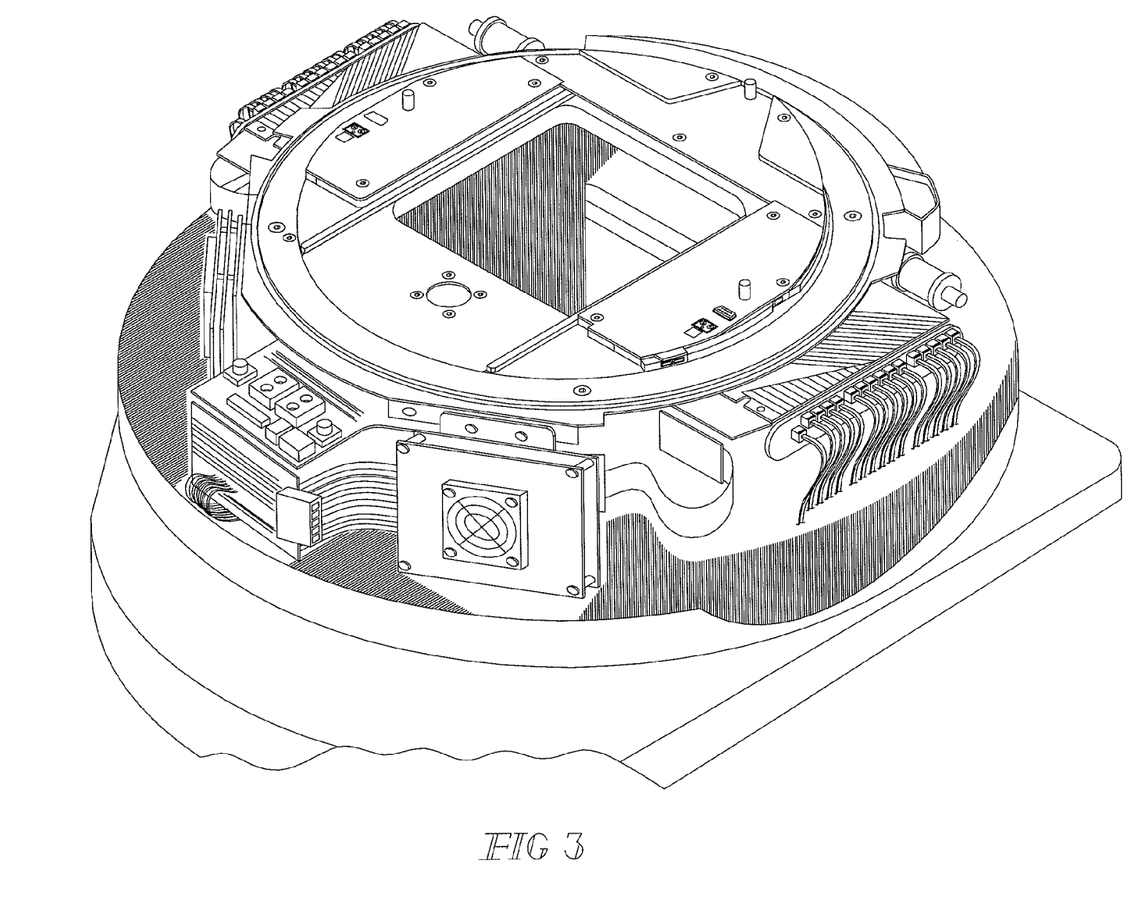
FIG. 3 illustrates a tungsten MLC used in application of megavoltage photon beams.
Figure 4A:
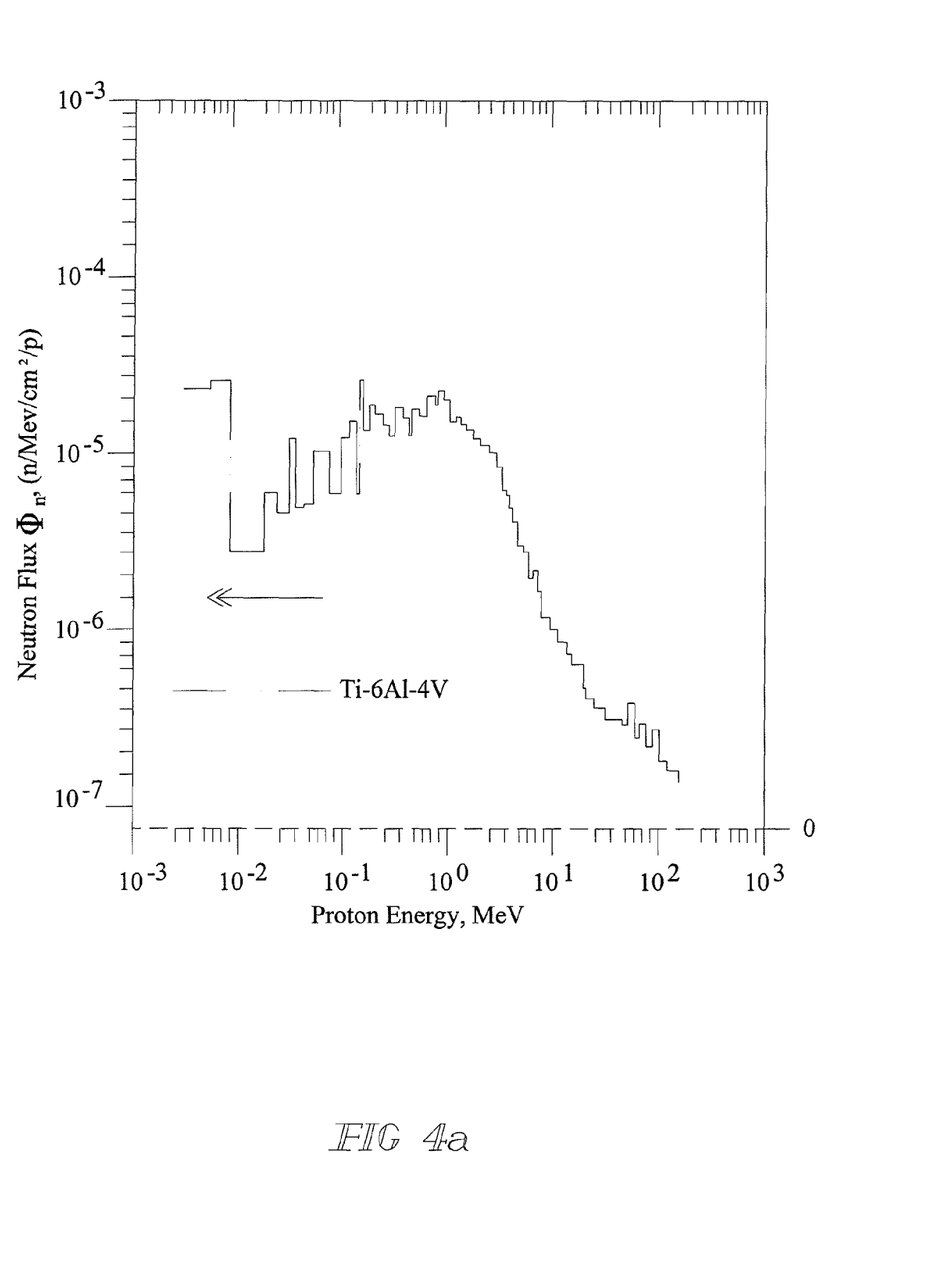
FIG. 4(a)-(d) illustrate neutron flux Φn from titanium alloy (Ti-6Al-4V), stainless steel, brass and tungsten alloy blocks during irradiation with 204 MeV proton beam. The spectra are computed for a detector of 0.5 cm radius placed at 10 cm distance along the beam axis from the downstream surface of the block imitating MLC.
Figure 4B:
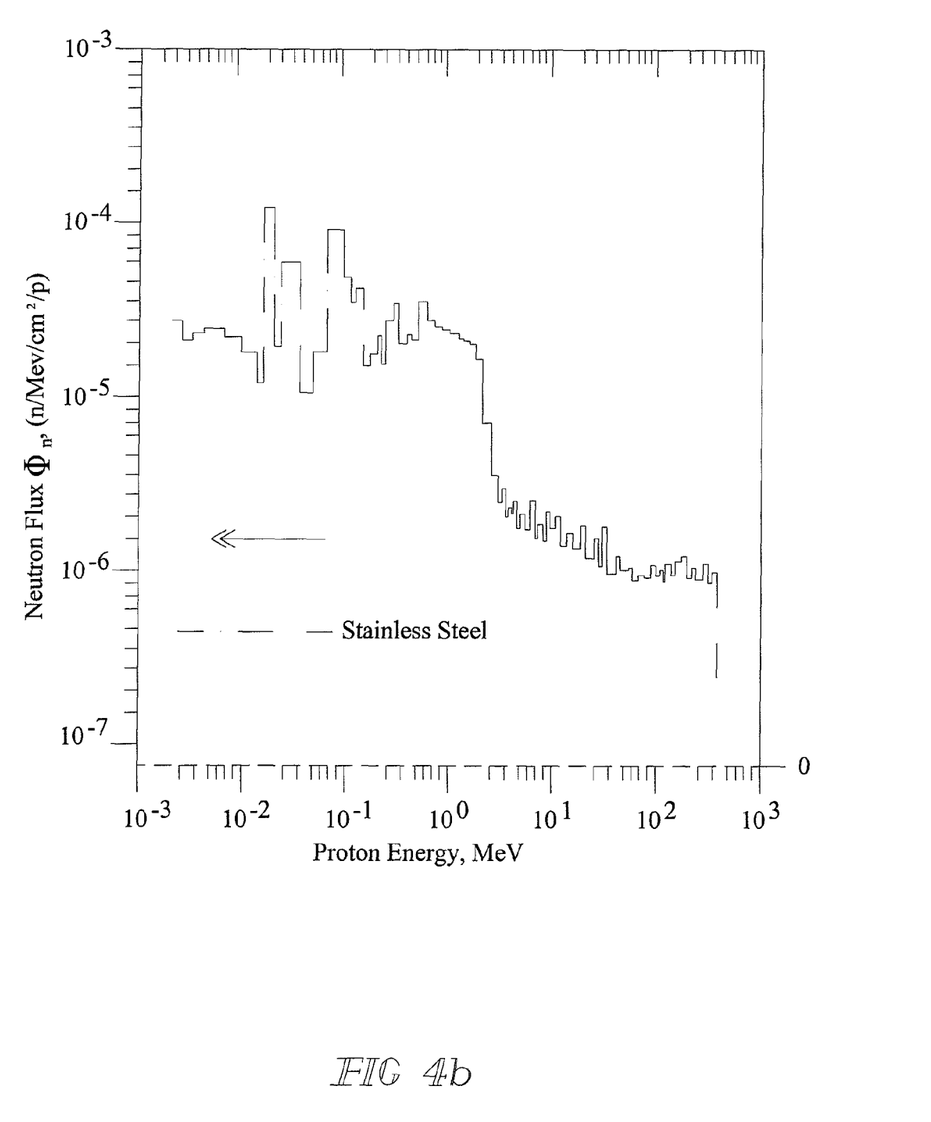
Figure 4C:
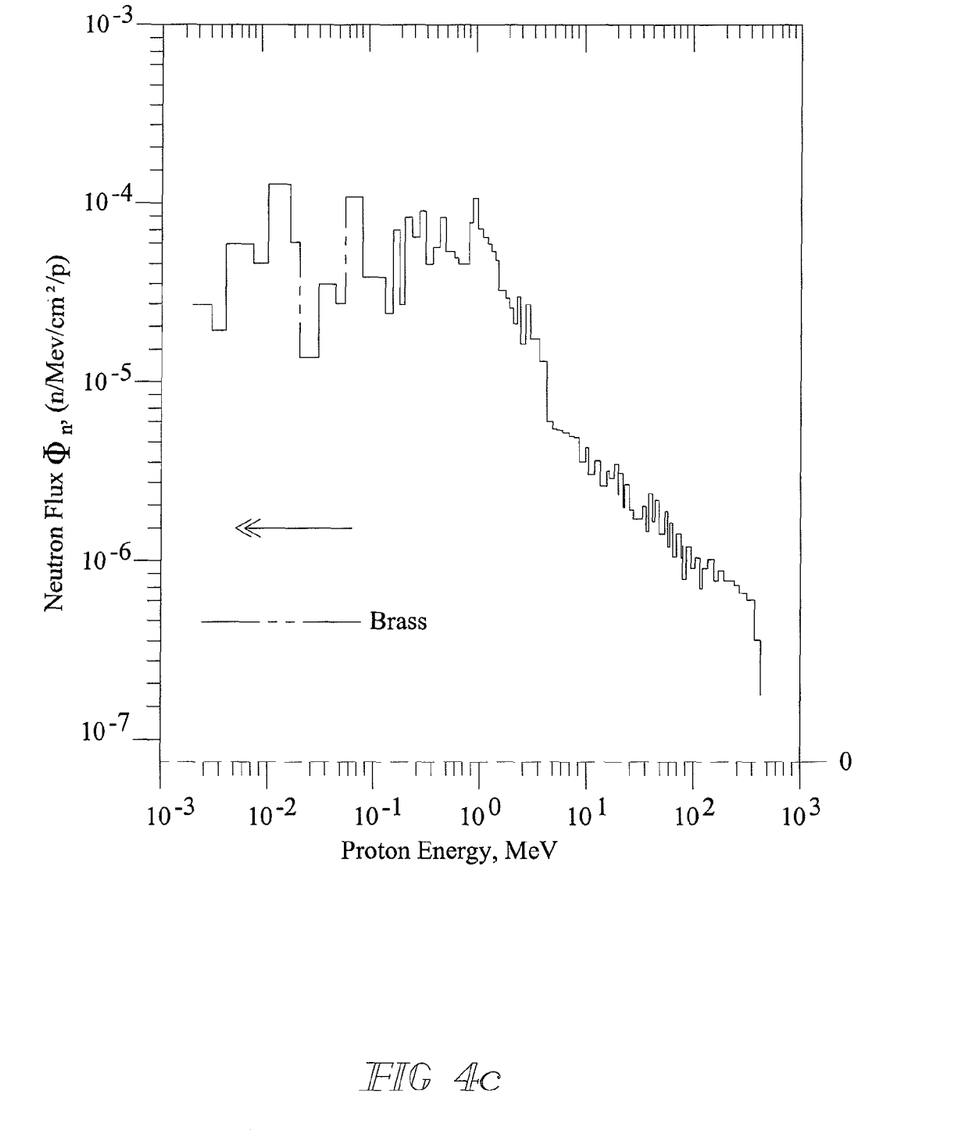
Figure 4D:
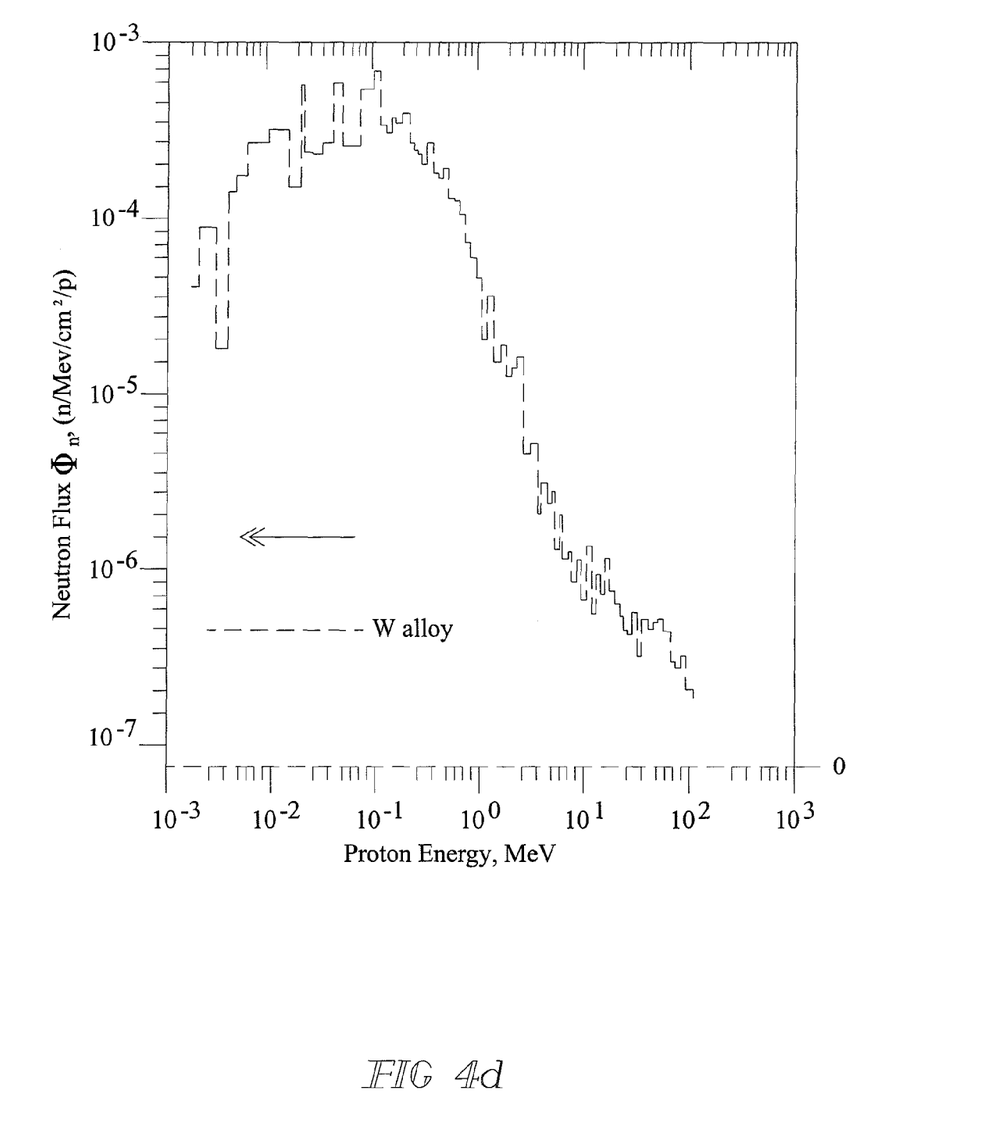
Figure 4E:
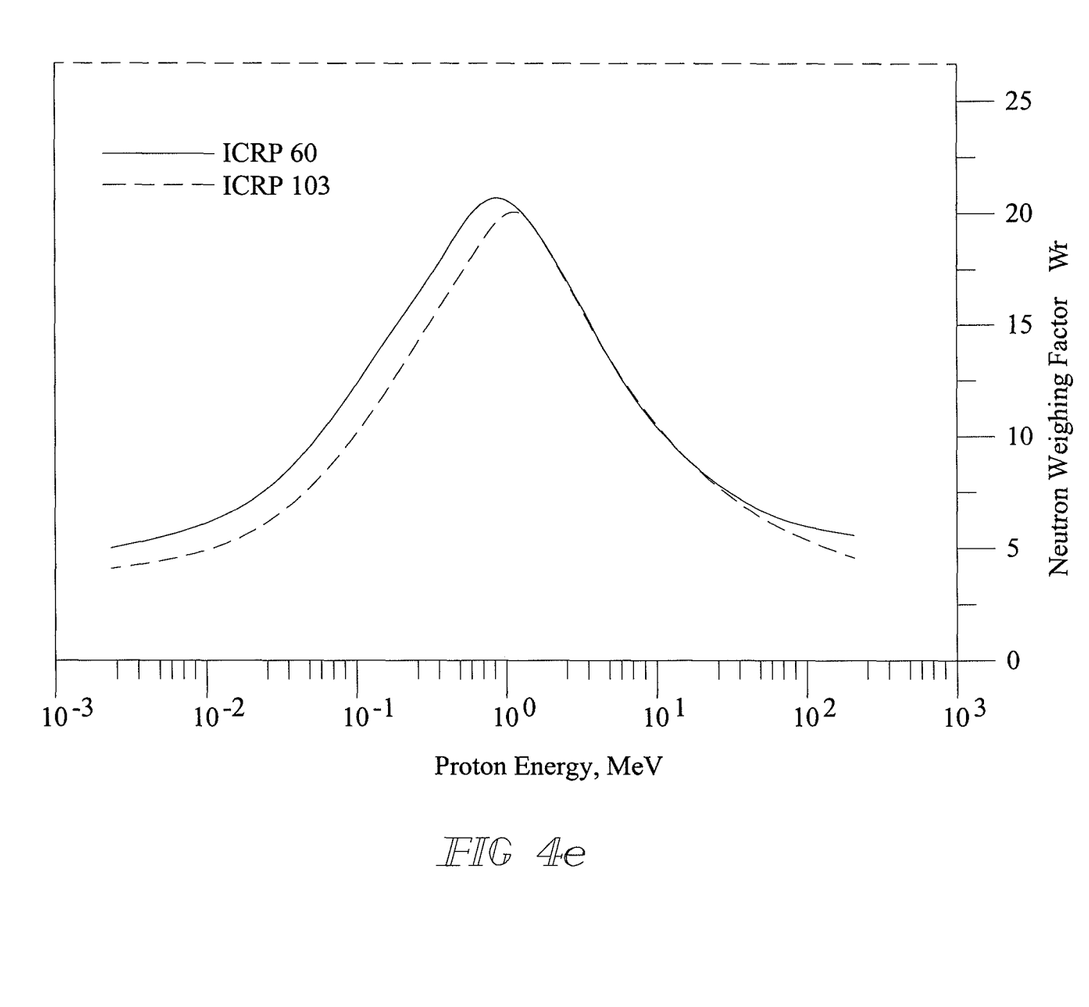
FIG. 4(e) illustrates neutron weighting factors from ICRP 60 and ICRP 103.

The typical position of electronics boards in an MLC designed for megavoltage therapy is laterally to the MLC block. FIG. 3 illustrates a typical megavoltage photon machine head including MLC electronics. The dose equivalent at small distances from the downstream MLC surface is higher than the dose from the middle level. While the contribution of the high-energy neutrons decreases with the lateral distance to the beam, the value of ambient dose equivalent becomes compatible. The values of the dose equivalent were estimated to be about 1.7 mSv·Gy$^{-1}$ at 10 cm distance and 1.2 mSv·Gy$^{-1}$ at 15 cm distance.

A set of experiments tests the MLC electronic circuit boards' stability toward SEU. Initial experiments with the components of the MLC circuit boards are carried out in proton beams available at the Indiana University (hereinafter sometimes IU) cyclotron Proton Dose Test Facility (hereinafter sometimes PDTF). The IU cyclotron accelerates protons to 205 MeV and degraded beam energies as low as 50 MeV are also available. Typical beam spot sizes are in the range of 1 to 10 cm, with available beam fluxes at 205 MeV between $10^7$ and $10^{11}$ protons cm$^{-2}$ s$^{-1}$. Upon completion of initial beam tests in PDTF, measurements are continued at the IU Health Proton Therapy Center (hereinafter sometimes IUHPTC, formerly Midwest Proton Radiotherapy Institute) in clinical proton beams produced by the IU cyclotron. A fixed beam line with a double-scattering technique and two gantries with uniform scanning beam are available at IUHPTC.

A prototype MLC based on minimization of the secondary neutron dose generated by a proton beam seeks to identify the optimal material for the MLC and the optimal geometry of the MLC, including the material specification, thickness and shape of leaves, to minimize the dose to a patient from secondary neutrons with Monte Carlo simulation of the primary proton beam and secondary neutron transport.

Monte Carlo simulations of the proton, neutron and X-ray transport in the geometry that is used for experiments with the MLC prototype, including selection of the optimal material and development of the concept of MLC prototype, are carried out using general-purpose particle transport code FLUKA. See, for example: Battistoni G, Muraro S, Sala P R, Cerutti F, Ferrari A, Roesler S, et al. The FLUKA code: Description and benchmarking. M. Albrow, R. Raja editors. Proceedings of the Hadronic Shower Simulation Workshop 2006, Fermilab 6-8 Sep. 2006, AIP Conference Proceedings. 2007; 896:31-49; and, Ferrari A, Sala P R, Fasso A, Ranft J. FLUKA: a multi-particle transport code. CERN 2005-10 (2005), INFN/TC__05/11, SLAC-R-773. Again, FLUKA is a fully integrated particle physics Monte Carlo simulation package widely used in experimental physics and engineering, shielding, detector design, dosimetry, medical physics and radiobiology. MCNPX code is used for calculations of the neutron transport and neutron-induced activation of phantom materials tracing the secondary particles for cross-reference and comparison. See, for example, Hughes H, Prael R, Little R. MCNPX—The LAHET/MCNP Code Merger, X-Division Research Note XTM-RN(U)97-012, LA-UR-97-4891 Los Alamos National Laboratory; 1997. PENELOPE Monte Carlo code (see, for example, Baro J, Sempau J, Fernandezvarea J M, Salvat F. Penelope—an Algorithm for Monte-Carlo Simulation of the Penetration and Energy-Loss of Electrons and Positrons in Matter. Nuclear Instruments & Methods in Physics Research Section B-Beam Interactions with Materials and Atoms. 1995; 100(1):31-46), is used for calculations of characteristic X-ray transport.

Titanium alloys as MLC materials is tested. The thickness of the MLC is determined for a set of clinical ranges. The material is selected based on the element composition. The simulations for selected materials determines the secondary neutron field during the treatment and activation of the materials. Final selection of optimum MLC materials and thicknesses are achieved by applying ALARA principle to the secondary neutron and photon dose and data on induced activity, and is limited by the mechanical properties of the titanium alloys.

The radiation tolerances of electronic circuits used for MLC controllers are determined and electronic placement for minimization of probability of soft errors caused by secondary neutron fluence is determined. Initial experiments with the components of the MLC circuit boards is carried out in proton beams at the IU PDTF and the IU cyclotron. The proton beam is blocked by the titanium absorbers to produce secondary neutron fields mimicking the expected secondary neutron fields for MLC clinical operations. The electronics circuit boards are placed in neutron fields to collect data on soft error rates encountered under typical MLC operating conditions. The computational data on neutron field and activation are used to predict electronic behavior and determine the placement and geometry of the circuit boards of the MLC controller and associated electronics boards.

Simulation was done with FLUKA Monte Carlo general purpose code. The details of the simulation model customization, methods of the neutron transport simulation activation of the MLC materials and neutron dose equivalent calculations are described in our recently published paper, where tungsten MLC was compared with the brass aperture. Moskvin V, Cheng C-W and J. Das I 2011 Pitfalls of tungsten multileaf collimator in proton beam therapy Medical Physics 38 6395-406. The simulation in this report is based on proton energy of 204 MeV, which is about the maximum energy from the IUCO cyclotron.

The thickness used for each block representing the MLC is equal to the proton range of 204 MeV proton in a given material plus an additional thickness to assure complete absorption of the proton beam in the block. The titanium alloy is represented by Ti-6Al-5V Grade 5 alloy annealed. The stainless steel block is given for illustrative purposes as one of the typical shielding design materials. The thicknesses of blocks were 10 cm for titanium alloy, and 5.54 cm for stainless steel. A tungsten alloy block of 3.3 cm corresponds to the equivalent thickness that titanium alloy block of one proton range plus additional material. This tungsten thickness is used in the next section where data on the neutron dose equivalent are analyzed. The tungsten block is 6.5 cm and 8.5 and 9 cm were considered in Moskvin V, Cheng C-W, Zhao Q and Das I J 2012 Comment on "Comparison of secondary neutron dose in proton therapy resulting from the use of a tungsten allow MLC or a brass collimator system." The brass aperture of 6.5 cm is currently used as a beam shaping device. Characterization of brass aperture was given in our paper Moskvin V, Cheng C-W and J. Das I 2011 Pitfalls of tungsten multileaf collimator in proton beam therapy Medical Physics 38 6395-406. Comparison of the neutron dose equivalent between various materials will be given at FIG. 5 below.

Neutron Flux and Neutron Dose Equivalent from Titanium Alloy MLC.

FIG. 4($a$) presents the spectra of neutrons $\Phi n(E)$ from titanium alloy (Ti-6Al-4V), stainless steel, brass and tungsten alloy blocks during irradiation with 204 MeV proton beam. The spectra computed for a detector of 0.5 cm radius placed at 10 cm distance along the beam axis from the downstream surface of the block imitating MLC. The neutron weighting factors from ICRP 1990 Recommendations of the International Commission on Radiological Protection ICRP Publication 60 (Oxford: Pergamon) and ICRP 2007 The 2007 Recommendations of the International Commission on Radiological Protection ICRP Publication 103 (Oxford: Pergamon) are given at FIG. 4($b$). FIG. 4($a$) shows that titanium alloy (Ti-6Al-4V) produces neutrons an order of magnitude less in the energy interval where the neutron weighting factor reaches a maximum compared to W.

Neutron dose equivalent results.calculated for the Ti-6Al-4V alloy block, stainless steel block, brass block, and tungsten alloy block are shown in FIG. 5. Again, titanium alloy produces less neutron dose equivalent at the patient location than do tungsten or stainless steel blocks. In proton therapy, patient surface is usually at 3-7 cm from the downstream surface of the compensator. It should be noted that utilization of the titanium alloy will reduce the dose equivalent from neutrons in comparison to current beam shaping devices, for example, a brass aperture as seen from FIG. 5.

Activation Analysis.

The results presented in Table 1 show that the residual activity of Ti alloy is only 5-7% of that from tungsten MLC after one year of irradiation and 40 days of cooling. On the other hand, stainless steel has 9-22% of the residual activity compared to W. Therefore, titanium alloy is more beneficial in the terms of the residual activity as a material for MLC.

TABLE 1

Activity of the irradiated part of the MLC material for various cooling times in percentage from the activity of the tungsten MLC of 6.5 cm thick at the same cooling times. The material was irradiated over 1 year. Table 2 illustrates contribution of isotopes from induced radioactivity in titanium alloy block irradiated over 1 year after 15 min cooling.

| Cooling Time | Titanium alloy Ti-6Al-4V, % of W MLC | Stainless Steel, % of W MLC |
|---|---|---|
| Immediately after beam off, <1 s | 4.86 | 8.588 |
| 15 min | 5.94 | 12.08 |
| 1 hour | 6.48 | 12.866 |
| 6 hours | 6.63 | 15.06 |
| 12 hours | 6.48 | 16.20 |
| 24 hours | 6.52 | 17.64 |
| 10 days | 4.97 | 21.14 |
| 40 days | 4.46 | 21.59 |

Almost 60% of the residual activity in Titanium alloy Ti-6Al-5V block irradiated over one year is due to $_{21}^{46}$Sc, with a half-life of 83.79 days, after 40 days of cooling. The rest 40% are from the other isotopes (Table 3). The isotopes $_{23}^{48}$V and $_{18}^{37}$Ar have relatively short half-lives and do not affect the long term storage requirement for the titanium alloy Ti-6Al-5V. Isotopes of $_{20}^{45}$Ca and $_{23}^{49}$V with half-life of 162.61 and 330 days, and tritium accumulation will require prolonged storage for cooling. However, the data on the total activity suggest that the absolute yield of these isotopes are small (1.4 and 1.5% of total activity after 15 min cooling time (see Table 2) of the alloy block irradiated over one year) and they will not made a major impact on the radiation environment around the MLC in storage. Taking into account that total activity in titanium alloy MLC is of about 6% of the activity in Tungsten MLC after one year irradiation, the impact of these isotopes could be considered as a minimal.

TABLE 2

Isotopes contributing to the residual activity of a unit irradiated volume of the Ti-6Al-5V alloy MLC. The irradiation duration is 1 year. Activity is given in % of total activity after 15 min of cooling. Here notations are h—hours, d—days, EC—electron capture β—beta decay, IT—internal conversion.

| Isotope | % of total Activity | Half-life, | Decay mode |
|---|---|---|---|
| $_{21}^{44}$Sc | 17.8 | 3.97 h | EC-100% |
|  |  | 58.61 h | IT-98%, EC-2% |
| $_{21}^{46}$Sc | 15.1 | 83.79 d | β-100% |
|  |  | 18.25 s | IT-100% |
| $_{22}^{45}$Ti | 14.0 | 184.3 m | EC-100% |
| $_{21}^{47}$Sc | 12.9 | 3.35 d | β-100% |
| $_{23}^{48}$V | 7.8 | 15.97 d | EC-100% |
| $_{21}^{43}$Sc | 4.4 | 3.89 h | EC-100% |

TABLE 3

Isotopes contributing to the residual activity of a unit irradiated volume of the Ti-6Al-5V alloy MLC. The irradiation duration is of 1 year. Activity is given in % of total activity after 40 days of cooling. Here notations are h—hours, d—days, EC—electron capture and β—beta decay, IT—internal conversion.

| Isotope | % of total activity | Half-life | Decay mode |
|---|---|---|---|
| $_{21}^{46}$Sc | 59.7 | 83.79 d | β-100% |
|  |  | 18.25 s | IT%-100% |
| $_{23}^{49}$V | 8.5 | 330 d | EC-100% |
| $_{20}^{45}$Ca | 7.8 | 162.61 d | β-100% |
| $_{23}^{48}$V | 7.6 | 15.97 d | EC-100% |
| $_{18}^{37}$Ar | 5.6 | 35.04 d | EC-100% |
| $_{1}^{3}$H | 2.8 | 12.32 y | β-100% |

The disclosures of all references cited herein are hereby incorporated herein by reference. Listing of references herein is not intended to be a representation that a complete search of all relevant art has been made, or that no more pertinent art than that listed exists, or that the listed art is material to patentability. Nor should any such representation be inferred.

What is claimed is:

1. A multi-leaf collimator for proton beam therapy, the collimator made from titanium.

2. The device of claim 1 further comprising an integrated circuit (IC) mounted adjacent the collimator, the IC subject to exposure to atomic particles.

3. The device of claim 2 further comprising an integrated circuit (IC) mounted adjacent the collimator, the IC subject to exposure to neutrons.

4. The device of claim 1 further comprising an integrated circuit mounted adjacent the collimator, the IC subject to exposure to atomic particles.

5. The device of claim 4 further comprising an integrated circuit (IC) mounted adjacent the collimator, the IC subject to exposure to neutrons.

6. A multi-leaf collimator for proton beam therapy, the collimator made from stainless steel including no tungsten.

7. The device of claim 6 further comprising an integrated circuit (IC) mounted adjacent the collimator, the IC subject to exposure to atomic particles.

8. The device of claim 7 further comprising an integrated circuit (IC) mounted adjacent the collimator, the IC subject to exposure to neutrons.

9. The device of claim 6 further comprising an integrated circuit mounted adjacent the collimator, the IC subject to exposure to atomic particles.

10. The device of claim 9 further comprising an integrated circuit (IC) mounted adjacent the collimator, the IC subject to exposure to neutrons.

11. A multi-leaf collimator for proton beam therapy, the collimator including no tungsten and no brass.

12. The device of claim 11 further comprising an integrated circuit (IC) mounted adjacent the collimator, the IC subject to exposure to atomic particles.

13. The device of claim 12 further comprising an integrated circuit (IC) mounted adjacent the collimator, the IC subject to exposure to neutrons.

14. The device of claim 11 further comprising an integrated circuit mounted adjacent the collimator, the IC subject to exposure to atomic particles.

15. The device of claim 14 further comprising an integrated circuit (IC) mounted adjacent the collimator, the IC subject to exposure to neutrons.

* * * * *